(12) United States Patent
Corcos et al.

(10) Patent No.: US 9,216,165 B2
(45) Date of Patent: Dec. 22, 2015

(54) COMBINATION OF A STATIN AND A TAXANE FOR THE TREATMENT OF GASTRIC CANCER

(75) Inventors: Laurent Corcos, Brest (FR); Catherine Le Jossic-Corcos, Brest (FR)

(73) Assignees: INSERM (Institut National de la Sante et de la Recherche Medicale), Paris (FR); Universite de Bretagne Occidentale, Brest Cedex (FR)

( * ) Notice: Subject to any disclaimer, the term of this patent is extended or adjusted under 35 U.S.C. 154(b) by 0 days.

(21) Appl. No.: 14/116,370

(22) PCT Filed: May 10, 2012

(86) PCT No.: PCT/EP2012/058684
§ 371 (c)(1), (2), (4) Date: Jan. 16, 2014

(87) PCT Pub. No.: WO2012/152885
PCT Pub. Date: Nov. 15, 2012

(65) Prior Publication Data
US 2014/0200269 A1    Jul. 17, 2014

(30) Foreign Application Priority Data
May 10, 2011    (EP) ..................................... 11305556

(51) Int. Cl.
| | | |
|---|---|---|
| *A01N 43/16* | (2006.01) | |
| *A61K 31/35* | (2006.01) | |
| *A01N 43/02* | (2006.01) | |
| *A61K 31/335* | (2006.01) | |
| *A61K 38/00* | (2006.01) | |
| *A61P 35/00* | (2006.01) | |
| *A61K 31/366* | (2006.01) | |
| *A61K 31/337* | (2006.01) | |

(52) U.S. Cl.
CPC ............. *A61K 31/366* (2013.01); *A61K 31/337* (2013.01)

(58) Field of Classification Search
None
See application file for complete search history.

(56) References Cited

U.S. PATENT DOCUMENTS

2002/0173538 A1* 11/2002 Shiao ..................... A61K 45/06
514/449
2009/0264377 A1* 10/2009 Einbond et al. ................. 514/26

OTHER PUBLICATIONS

Holstein et al., Synergistic Interaction of Lovastatin and Paclitaxel in Human Cancer Cells, Dec. 2001, Molecular Cancer Therapeutics, vol. 1, pp. 141-149.*
Sadeghi-Aliabadi et al.; "Evaluation of Synergistic Cytotoxicity of Co-Administration of Taxol and Atorvastatin on MDA-MB-468 Cell Line"; Anticancer Research, vol. 38, No. 5C, Sep. 2008, p. 3467 and 8th International Conference of Anticancer Research; Kos Isl, Greece; Oct. 17-22, 2008.
Holstein et al.; "Synergistic Interaction of Lovastatin and Paclitaxel in Human Cancer Cells"; Molecular Cancer Therapeutics; vol. 1, No. 2; Dec. 1, 2001; pp. 141-149.

* cited by examiner

*Primary Examiner* — Kortney L Klinkel
*Assistant Examiner* — Tori M Strong
(74) *Attorney, Agent, or Firm* — Whitham, Curtis, Christofferson & Cook, P.C.

(57) ABSTRACT

The present invention relates to a combination of (i) a statin, and (ii) a taxane, for simultaneous or sequential use in the treatment of a patient suffering from solid tumor, e.g. a gastric cancer. The present invention also provides a statin, for use in a method for enhancing sensitivity of a patient suffering from a solid tumor to a taxane.

3 Claims, 10 Drawing Sheets

COMBINATION OF A STATIN AND A TAXANE FOR THE TREATMENT OF GASTRIC CANCER

RELATED APPLICATION

Figure 1:
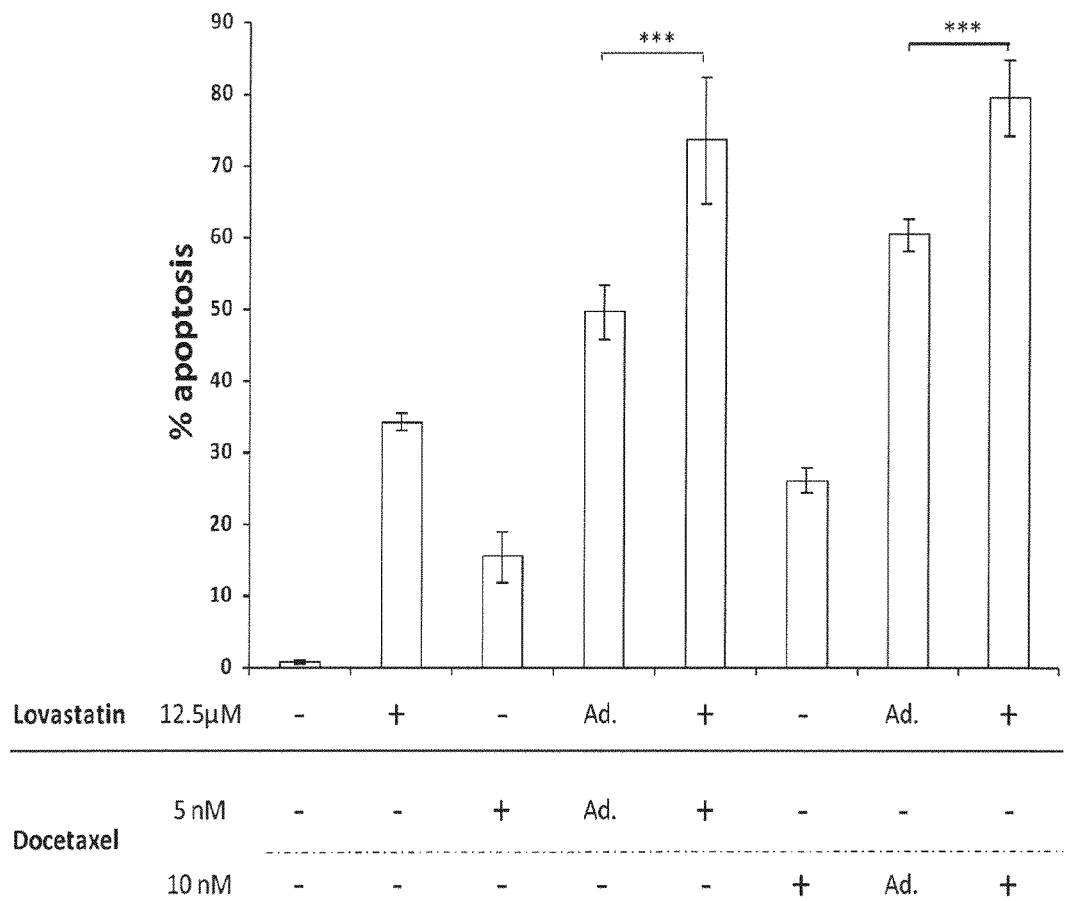

The present application claims priority to European Patent Application No. EP 11 305 556, which was filed on May 10, 2011. The European patent application is incorporated herein by reference in its entirety.

FIELD OF THE INVENTION

The present invention relates to a combination of (i) a statin, and (ii) a taxane, for the simultaneous or sequential use in the treatment of a patient suffering from a solid tumor, e.g. a gastric cancer. The present invention also provides a statin, for use in a method for enhancing sensitivity of a patient suffering from solid tumor to a taxane.

BACKGROUND OF THE INVENTION

Gastric cancer is mostly associated with poor survival and ranks 5 in Europe in terms of incidence. Because it is often detected at late stages, available treatments are mostly inefficient.

Microtubule targeting agents of the taxane class, like docetaxel, have been used for almost a decade to treat refractory breast cancer, and they have also been foreseen to treat gastric cancer. However, only few patients could benefit from docetaxel treatment, mostly because of severe side effects (Baker, Ajani et al. 2009). Nevertheless, above 80 clinical trials recorded at the NIH still evaluate—or will aim at doing so when recruitment will be completed—docetaxel as an anticancer agent in combination with other chemotherapeutic agents, including 5-fluorouracile, cisplatin, capecitabin, epirubicin, Gleevec®, bevacizumab, among several others. Hence, docetaxel is still believed to be promising for the treatment of gastric cancer.

Statins are used as anti-hypercholesterolemia drugs, but they also bear potential as either cancer preventive or adjuvant therapies (Demierre, Higgins et al. 2005). There has been some dispute in the literature concerning the chemoprevention statins may exert on cancer occurrence (Bjerre and LeLorier 2001; Katz 2005). By contrast, analyses in experimental models have mostly converged towards the concept that statins may increase the efficacy of cancer cell killing triggered by several classes of drugs and used to target various types of cancer cells (Graaf, Richel et al. 2004; van der Spek, Bloem et al. 2009; Sane, Mynderse et al. 2010; Zheng, Cui et al. 2010). Hence, combinations of various statins with DNA damaging agents like topoisomerase inhibitors, cisplatin or 5-fluorouracile have shown increased cell death, reduced tumour growth or reduction in metastases (Agarwal, Bhendwal et al. 1999; Kozar, Kaminski et al. 2004; Martirosyan, Clendening et al. 2010; Taylor-Harding, Orsulic et al. 2010).

The molecular mechanisms triggered in response to statins or docetaxel have been deeply investigated in cell culture and in animal models. Both drugs are capable of triggering apoptosis (Schimming, Mason et al. 1999; Sassano and Platanias 2008). Their sub-cellular targets may be either shared or quite distinct. Docetaxel promotes microtubule assembly and stabilize the polymers against depolymerization, thereby inhibiting microtubule dynamics. As a result, mitotic progression is restricted, which leads to inhibition of cell proliferation. Statins have no reported effects of the activity of the mitotic spindle. Docetaxel triggers the degradation of the anti-apoptotic Bcl-2 protein through increased phosphorylation, and statins suppress the Bcl-2 protein (Wong, Dimitroulakos et al. 2002). Both docetaxel and statins inhibit angiogenesis, although this may depend on the administered dose for statins. Statins can induce the cell cycle inhibitor protein p21, whereas docetaxel has no effect on p21 expression (Gray-Bablin, Rao et al. 1997; Demidenko, Halicka et al. 2005). One study had shown that the combination of paclitaxel and lovastatin had a synergistic effect on apoptosis of leukemia cells (Holstein and Hohl 2001).

However, leukaemia is clearly a quite different cancer type than solid tumors. In particular, the local microenvironment of cancer cells is completely different in a non solid tumor such as leukaemia, in which cancer cells freely circulate and do not form a sort of solid organ, and in solid tumors, in which the tumor forms a complex and organized entity, resulting in complex interactions between various cancer cells types and reduced accessibility of at least some cancer cells to drugs due to their localization in the tumor solid mass;

To conclude, taxanes and statins have been tested as anti-cancer therapy but none of the above categories of agents have proven liable to completely treat individuals afflicted with cancer, and specially solid tumors such as gastric cancers, which are notably associated with poor prognosis. Thus, there is a need for new therapeutic alternatives that could provide new perspectives in particular in gastric cancer treatment.

SUMMARY OF THE INVENTION

The present invention relates to a combination of a statin, and of a taxane for simultaneous or sequential use in the treatment of a patient suffering from solid tumor, and in particularly from gastric cancer. The present invention also provides a statin, for use in a method for enhancing sensitivity of a patient suffering from solid tumor to a taxane.

DETAILED DESCRIPTION OF THE INVENTION

The present invention arises from the unexpected finding by the inventors that an antimitotic agent, such as taxane (docetaxel), acts synergistically with a statin (lovastatin), to promote cancer cell apoptosis and prevent cell proliferation. This association proved to be effective in vitro in the human gastric cancer cell line HGT-1. Marker expression showed that both compounds suppressed the anti-apoptotic form of the Mcl-1 protein, but induced the cell cycle inhibitor protein p21, although the effect of docetaxel was rather limited, resulting in a higher sensitizing effect. In addition, docetaxel-resistant derivatives of HGT-1 cells were sensitive to statins, even more than HGT-1 cells. As a whole, this novel drug combination was more efficient at inducing apoptosis than either drug alone in HGT-1 sensitive cells. As shown in FIG. 1, the exposure to both drugs (lovastatin and docetaxel) had a synergistic effect (up to 80% apoptosis), when compared to the effect expected from the addition (Ad) of apoptosis % obtained for the drugs used as single agents. Lovastatin was also able to overcome the acquired resistance to docetaxel, a result showing promise for the treatment of docetaxel-resistant cells, potentially arising following long term treatment.

Lovastatin strongly suppressed expression of mRNAs encoding cyclins B1 and D1, aurora kinases A and B, and survivin alone or combined with docetaxel. Although docetaxel strongly induced the survivin protein, lovastatin, alone or in combination, strongly suppressed expression of all these proteins. Hence, this drug combination acted to suppress cell division and increase apoptosis of HGT-1 cells.

Combination of a Taxane with a Statin, for Use in the Treatment of Solid Tumor

Therefore, the present invention provides a combination of
i. a taxane; and
ii. a statin;
for simultaneous or sequential use in the treatment of a solid tumor.

In a preferred embodiment the solid tumor is a gastric cancer, cervix cancer, colon cancer, and liver cancer.

The present invention also provides a statin, for use in a method for enhancing sensitivity of a patient suffering from solid tumor to a taxane.

In a preferred embodiment the solid tumor is a gastric cancer

In its broadest meaning, the term "treating" or "treatment" refers to reversing, alleviating, inhibiting the progress of the disorder or condition to which such a term applies, or one or more symptoms of such a disorder or condition.

By "taxane", is meant an anti-mitotic agent that is capable of slowing down and/or inhibiting mitosis. The taxanes are diterpenes that were originally derived from plants of the genus Taxus (yews). Now, they are usually synthesized. Taxanes have been used to produce various chemotherapy drugs such as, e.g., Paclitaxel (Taxol), Docetaxel (Taxotere) and Cabazitaxel. These taxanes, and especially Docetaxel (Taxotere), are preferred chemotherapeutic drugs that can be used in the frame of the present invention.

The term "Docetaxel" herein includes both naturally derived and related forms and chemically synthesized compounds or derivatives thereof with antineoplastic properties.

In addition, other derivatives of taxane are mentioned in" Synthesis and Anticancer Activity of Taxol other Derivatives, "D. G. l. Kingston et al., Studies in Organic Chemistry, vol. 26, entitled "New Trends in Natural Products Chemistry" (1986), Atta-ur-Rabman, P. W. le Quesne, Eds. (Elvesier, Amsterdam 1986), pp 219-235 are explicitly included here.

By "statin", is meant HMG-CoA reductase inhibitors which form a class of hypolipidemic agents, used as pharmaceuticals to lower cholesterol levels in people with or at risk for cardiovascular disease. They cause cholesterol lowering by inhibiting the enzyme HMG-CoA reductase, an enzyme involved in the first step of cholesterol synthesis. Inhibition of this enzyme in the liver stimulates the LDL-receptors, which results in an increased clearance of LDL from the bloodstream and a decrease in blood cholesterol levels.

In a preferred embodiment of the present invention, the statin is selected from the group consisting of atorvastatin (marketed as Lipitor and Torvast), cerivastatin, fluvastatin (Lescol), lovastatin (Mevacor, Altocor, Altoprev), pravastatin (Pravachol, Selektine, Lipostat), pitavastatin (Livalo, Pitava), simvastatin (Zocor, Lipex), rosuvastatin (Crestor) and chemical derivatives thereof, including the pharmaceutical effective salts, solvates, esters and adducts thereof.

In most preferred embodiment of the present invention, the statin is lovastatin.

Examples of statin and HMG-CoA reductase inhibitors are also described in a review [Pfefferkorn J A. Novel 3-hydroxy-3-methylglutaryl-coenzyme A reductase inhibitors: a patent review. Expert Opin Ther Pat. February 2011; 21(2):187-203] and is incorporated here by reference.

A further aspect of the invention relates to a method for treating solid tumors, comprising administering a subject in need thereof with amounts of a statin compound and a taxane compound.

As used herein, the term "subject" denotes a human affected by a solid tumor.

As used throughout the present specification, the term "solid tumor" refers to any type of malignant tumor (i.e. non benign tumor). The malignant tumor may correspond to a primary tumor or to a secondary tumor (i.e. a metastasis).

More precisely "solid tumor" are masses of abnormal tissue that originate in organs or soft tissues that typically do not include fluid areas and cysts. Solid tumors are typically named after the types of cells that compose them. The solid tumor may correspond to a solid malignant tumor such as e.g. a carcinoma, an adenocarcinoma, a sarcoma, a melanoma, a mesothelioma or a blastoma. Leukemia is not considered a solid tumor because it is a cancer of the blood.

The solid tumor preferably corresponds to a solid malignant tumor that is an epithelial cancer, e.g. a carcinoma or an adenocarcinoma involving malignant proliferation of epithelial tissue cells.

The solid tumor most preferably corresponds to a stomach cancer (or gastric cancer in particular gastric carcinoma, signet ring cell carcinoma, gastric lymphoma (MALT lymphoma)), a breast cancer, a cervix cancer, a pancreatic cancer, an ovary cancer, a head-and-neck cancer, a colon cancer, a rectal cancer, a liver cancer (in particular a hepatocarcinoma), a prostate cancer, a bladder cancer and a Non-Small-Cell lung carcinoma.

In the preferred embodiment of the invention the "solid tumor" is gastric cancer (also called stomach cancer), cervix cancer, colon cancer, and liver cancer (in particular a hepatocarcinoma).

The gastric cancer commonly referred to as stomach cancer, or gastric carcinoma or adenocarcinoma of the stomach, is a common cancer of the digestive tract worldwide, which occurs most frequently in men over 40 years old. Gastric cancer diagnosis is often delayed because symptoms may not occur in the early stages of the disease and because it is often detected at late stages, available treatments are mostly inefficient.

As used herein, the term "active ingredients of the invention" is intended to refer to the taxane compound and the statin compound as defined above.

The active ingredients of the invention may be administered in the form of a pharmaceutical composition, as defined below.

Preferably, the active ingredients of the invention are administered in a therapeutically effective amount.

By a "therapeutically effective amount" is meant a sufficient amount of the active ingredients of the invention to treat a solid tumor at a reasonable benefit/risk ratio applicable to any medical treatment.

In a preferred embodiment, the taxane compounds of the invention are preferably administered by the intravenous route, the statin compound of the invention are preferably administered by the oral route.

According to the invention, the active ingredients of the invention may be administered as a combined preparation for simultaneous, separate or sequential use in the treatment of solid tumor.

Since association of statins and taxanes had a synergistic effect on gastric cancer cells, the taxane drug can advantageously be used at lower doses than in a treatment regimen wherein it is administered alone.

Therefore, in a preferred embodiment of the combination according to the invention, the taxane drug is for use at a low dose, i.e. at a lower dose than the dose recommended when said drug is administered without said statin.

The skilled in the art can immediately determine a low dose for a given taxane drug. Such a low dose notably depends on the cancer to be treated and on the therapeutic protocol.

In the frame of the present invention, by "low dose" is meant a dose that is inferior to the recommended dose that would be given to the patient when the taxane is administered in the absence of the statin. Said low dose is preferably inferior by at least 10%, 15%, 20%, 25%, 50% or 75% to the recommended dose when combined to the usual therapeutic dose of statin.

The recommended dose that would be given to the patient when the taxane is administered in the absence of the statin is known to the skilled in the art. Such a recommended dose can, for example, be found in the information provided by the authorities delivering marketing authorizations (e.g. in the EPARs published by the EMEA).

As an illustrative example, it will be described here below what is meant by a low dose of docetaxel.

For example, for the treatment of patients with locally advanced or metastatic breast cancer, the recommended dose of docetaxel is 100 mg/m$^2$ in monotherapy. Therefore, a low dose of docetaxel, in the frame of the treatment in monotherapy of patients with locally advanced or metastatic breast cancer, is a dose inferior to 100 mg/m$^2$, preferably inferior to 90 mg/m$^2$, 75 mg/m$^2$, 50 mg/m$^2$ or 25 mg/m$^2$.

In contrast to this, when docetaxel is used as an adjuvant treatment of operable node-positive and node-negative breast cancer, the recommended dose of docetaxel is 75 mg/m$^2$ administered 1-hour after doxorubicin 50 mg/m$^2$ and cyclophosphamide 500 mg/m$^2$ every 3 weeks for 6 cycles (TAC regimen). More generally, docetaxel is usually administered at 75 mg/m$^2$ when associated with another drug (e.g. endoxan or capecitabin) or when the patient is at risk of not tolerating an aggressive chemotherapy. Therefore, a low dose of docetaxel, in the frame of a TAC regimen when associated with another drug or when the patient is believed not to tolerate an aggressive chemotherapy, is a dose inferior to 75 mg/m$^2$, preferably inferior to 50 mg/m$^2$, 40 mg/m$^2$, 30 mg/m$^2$ or 15 mg/m$^2$.

As another illustrative example, it will be described here below what is meant by a low dose of paclitaxel (Taxol).

Paclitaxel is usually administered at 80 or 90 mg/m$^2$ once a week (e.g. on days 1, 8, 15, and then on day 28 and each following week, optionally in combination with other drugs). Therefore, a low dose of paclitaxel is a dose inferior to 80 mg/m$^2$, preferably inferior to 70 mg/m$^2$, 60 mg/m$^2$, 50 mg/m$^2$, 40 mg/m$^2$ or 20 mg/m$^2$.

The dose for administration envisaged for the statin may be for example from 10 to 100 mg per day, preferably from 20 to 80 mg per day, more preferably from 40 to 80 mg per day.

In a preferred embodiment, the taxane of the invention is preferably administered by the intravenous route, the statin of the invention is preferably administered by the oral route.

Pharmaceutical Compositions According to the Invention

The present invention also provides a pharmaceutical composition comprising:
  i. a taxane (as defined here above),
  ii. a statin (as defined here above); and
  iii. a pharmaceutically acceptable carrier.

Pharmaceutical compositions formulated in a manner suitable for administration to humans are known to the skilled in the art. The pharmaceutical composition of the invention may further comprise stabilizers, buffers, etc.

The compositions of the present invention may, for example, be formulated and used as tablets, capsules or elixirs for oral administration, suppositories for rectal administration, sterile solutions or suspensions for administration by injection.

The choice of the formulation ultimately depends on the intended way of administration, such as e.g. an intravenous, intraperitoneal, subcutaneous or oral way of administration, or a local administration via tumor injection.

The pharmaceutical composition according to the invention may be a solution or suspension, e.g. an injectable solution or suspension. It may for example be packaged in dosage unit form.

In a preferred embodiment, the taxane of the invention is preferably administered by the intravenous route, the statin of the invention is preferably administered by the oral route.

The present invention also provides a pharmaceutical composition comprising:
  i. a taxane (as defined here above),
  ii. a statin (as defined here above); and
  iii. a pharmaceutically acceptable carrier.
  for use in the prevention or the treatment of solid tumor in a patient in need thereof.

In preferred embodiment, the solid tumor is gastric cancer, cervix cancer, colon cancer, and liver cancer.

The invention will be further illustrated by the following figures and examples. However, these examples and figures should not be interpreted in any way as limiting the scope of the present invention.

FIGURES

FIG. 1: Apoptosis induction by lovastatin and docetaxel in HGT-1 gastric cancer cells HGT-1 cells were treated with 12.5 µM lovastatin or with 5 or 10 nM docetaxel alone, or in combination for 48 h. Apoptosis was determined by Hoechst 33342 staining. Values are means±S.D. (n=6). Ad: expected percentage from additive effects, addition of % apoptosis from lovastatin (12.5 µM)+ docetaxel (5 or 10 nM). *** P<0.001 compared with the numerical addition of individual treatments (Student's t test).

Figure 2:
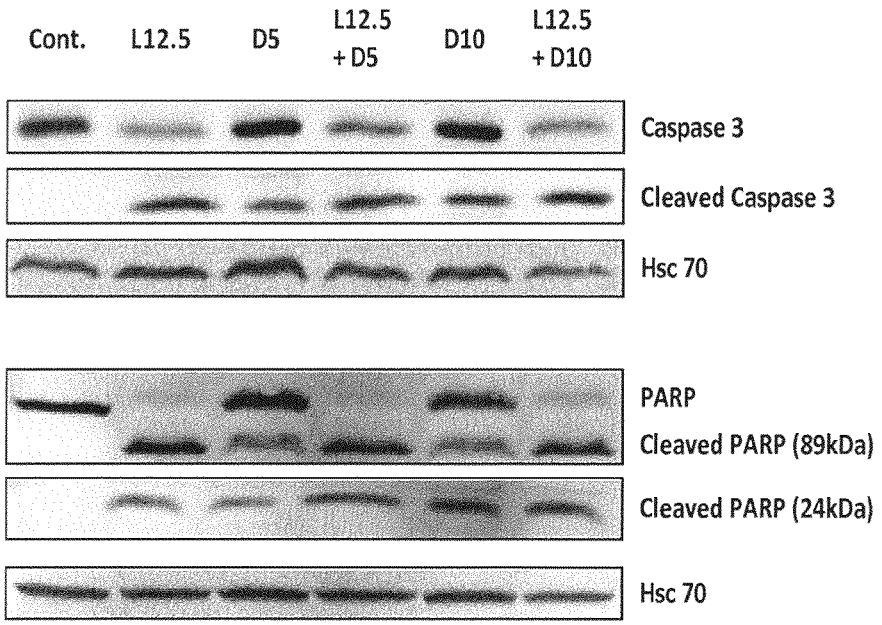
Figure 2:
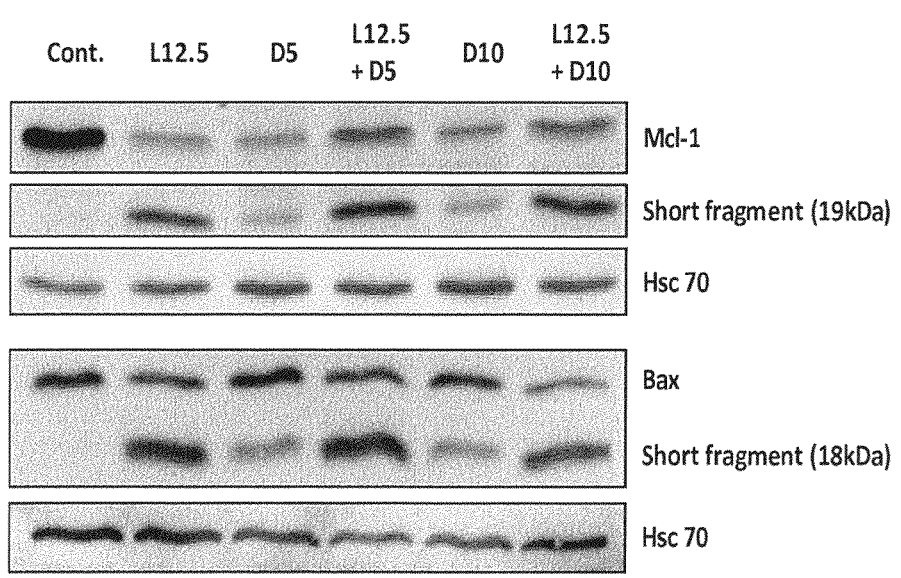

FIG. 2 effect of lovastatin and docetaxel on Mcl-1 and Bax, caspase-3 and PARP protein levels HGT-1 cells were treated with 12.5 µM lovastatin (L) or with 5 or 10 nM docetaxel (D) alone or in combination for 48 h. Protein levels were analyzed by western-blotting. Hsc70 was used as a loading control. The results are representative of three experiments with similar results.

Figure 3:
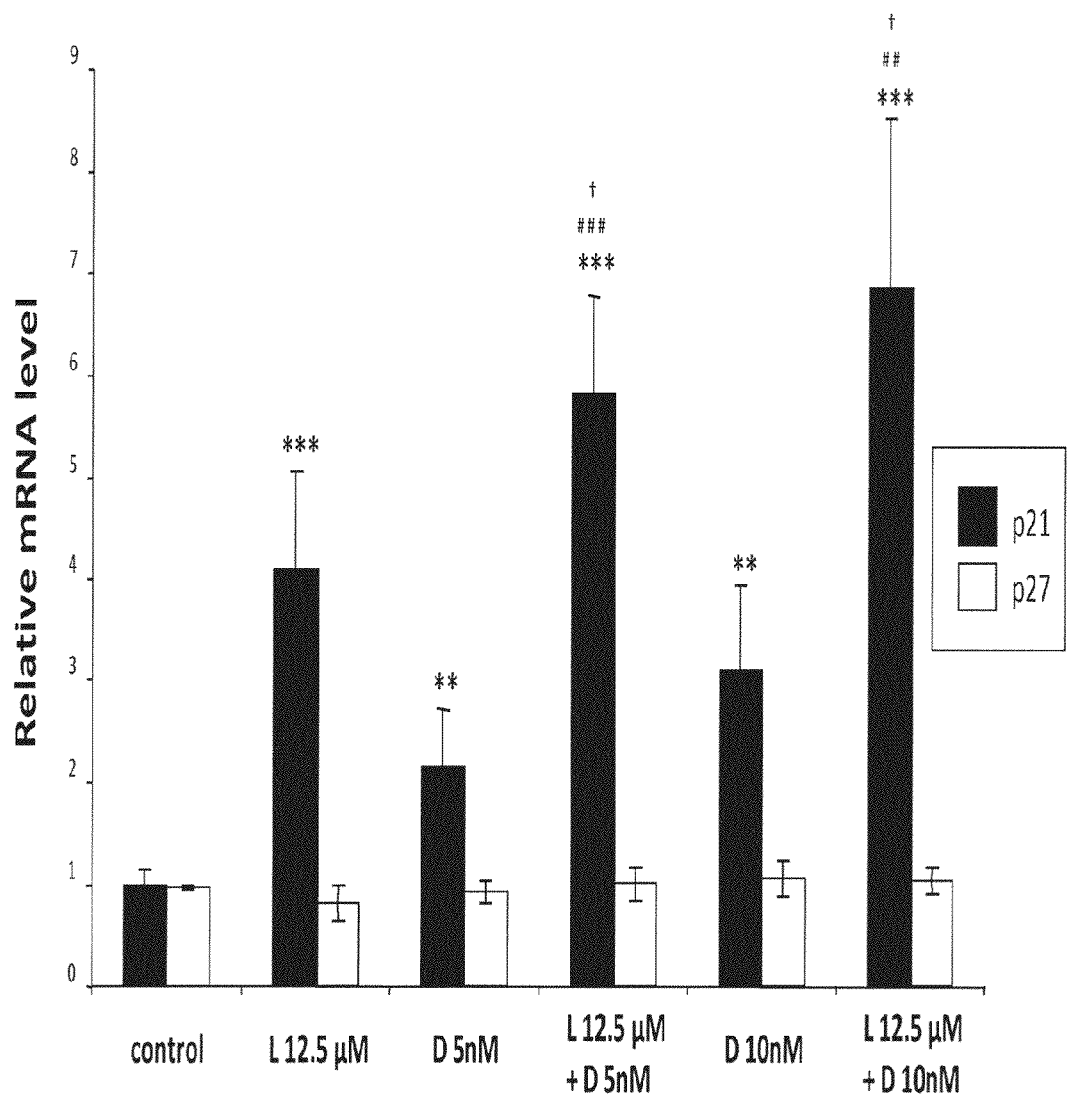

FIG. 3 Effect of lovastatin and docetaxel on p21 and p27 gene expression

HGT-1 cells were treated with 12.5 µM lovastatin (L) or with 5 or 10 nM docetaxel (D) alone or in combination for 48 h. (A) p21 and p27 mRNA levels were analyzed by RT-real time PCR. Relative mRNA levels were normalized to GAPDH mRNA levels. Values are means±S.D. (n=4). * compared with control, # compared with docetaxel treatment, † compared with lovastatin treatment. One symbol: P<0.05, two symbols: P<0.01, three symbols: P<0.001 (Student's t test).

Figure 4A:
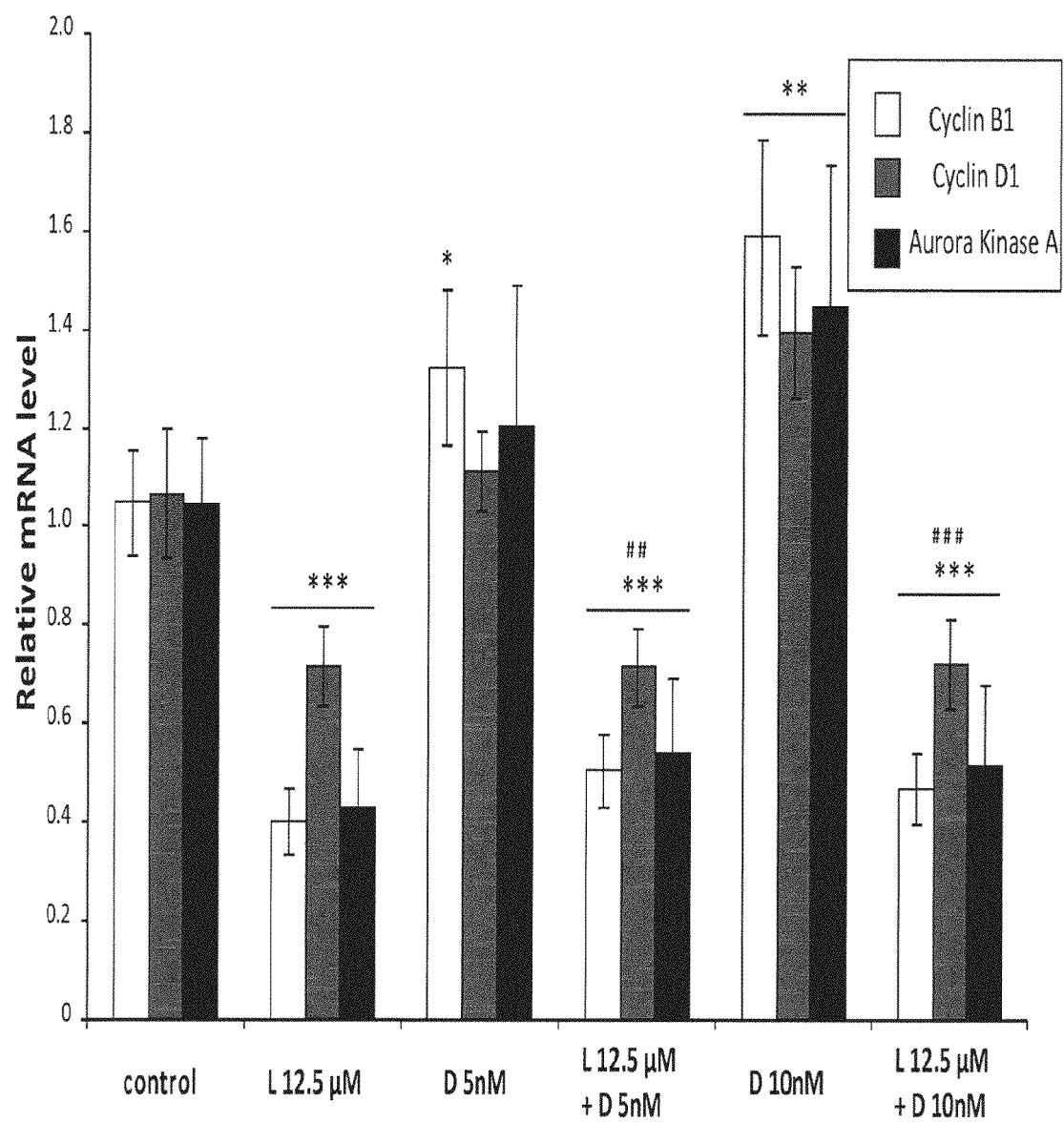
Figure 4:
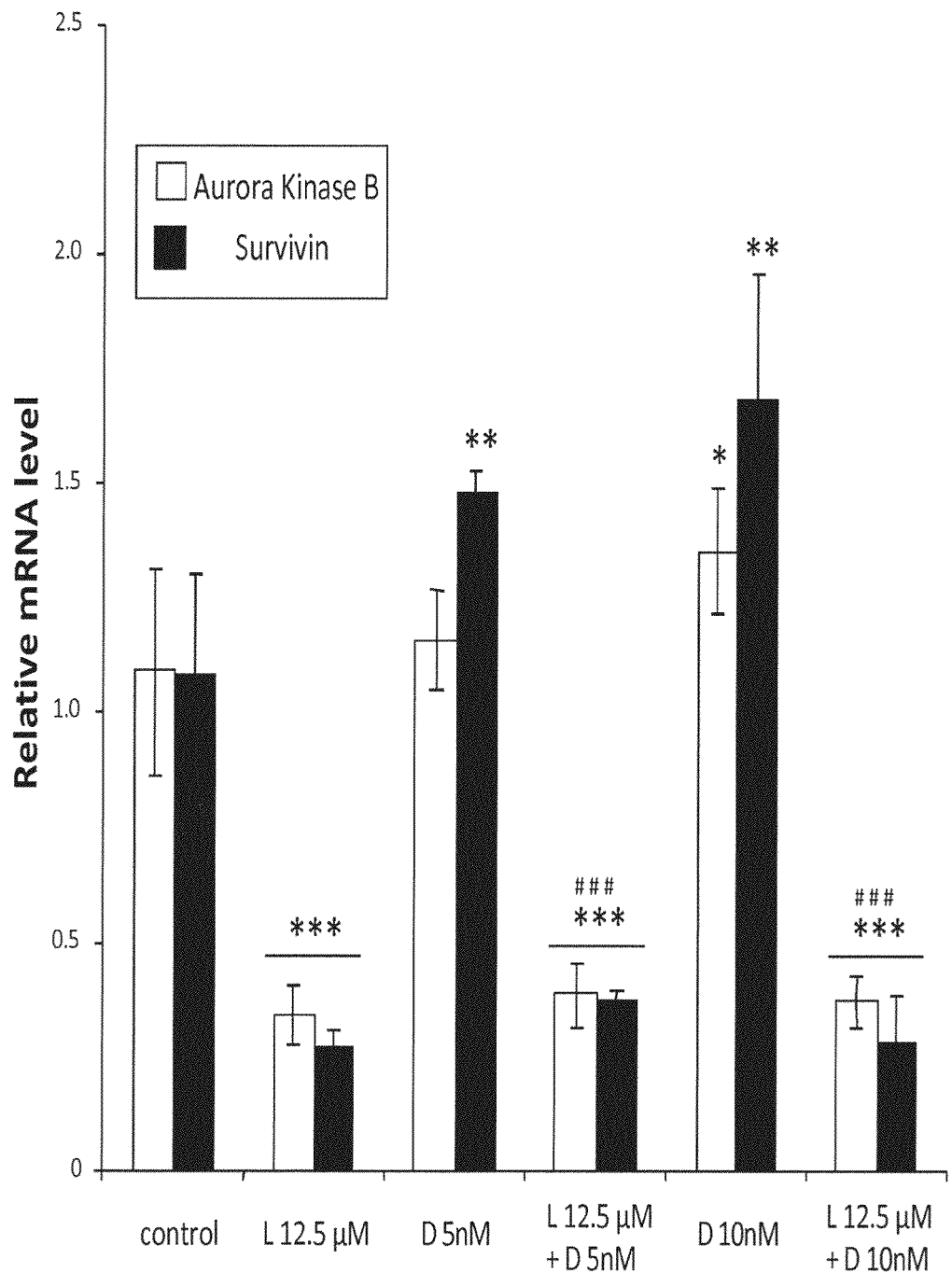
Figure 4:
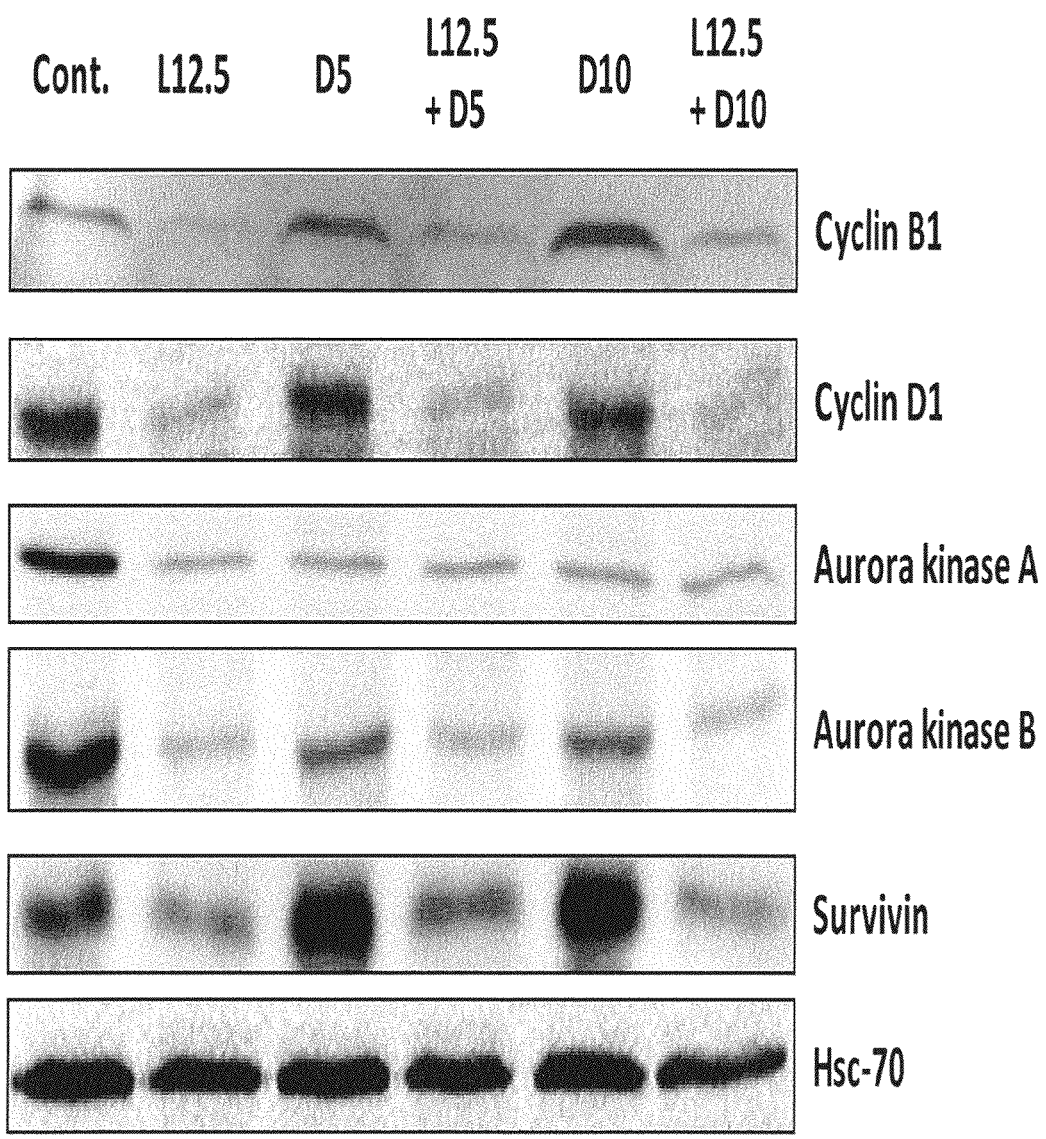

FIG. 4 Effect of lovastatin and docetaxel on expression of genes involved in the initiation and progression of mitosis, cytokinesis and MAP kinases signalling pathway HGT-1 cells were treated with 12.5 µM lovastatin (L) or with 5 or 10 nM docetaxel (D) alone or in combination for 48 h. Cyclin D1, cyclin B1, aurora kinase A (A), aurora kinase B and survivin (B) mRNA levels were analyzed by RT-real time PCR. Relative mRNA levels were normalized to P0 mRNA levels. Values are means±S.D. (n=4). * compared with control, # compared with docetaxel treatment, † compared with lovastatin treatment. One symbol: P<0.05, two symbols: P<0.01, three symbols: P<0.001 (Student's t test). (C) Cyclin B1, D1, aurora kinase A,-B and survivin protein levels were analyzed by western-blotting. Hsc70 was used as a loading control. Hsc70 was used as a loading control. The western blotting analyses are representative of three experiments with similar results.

Figure 5:
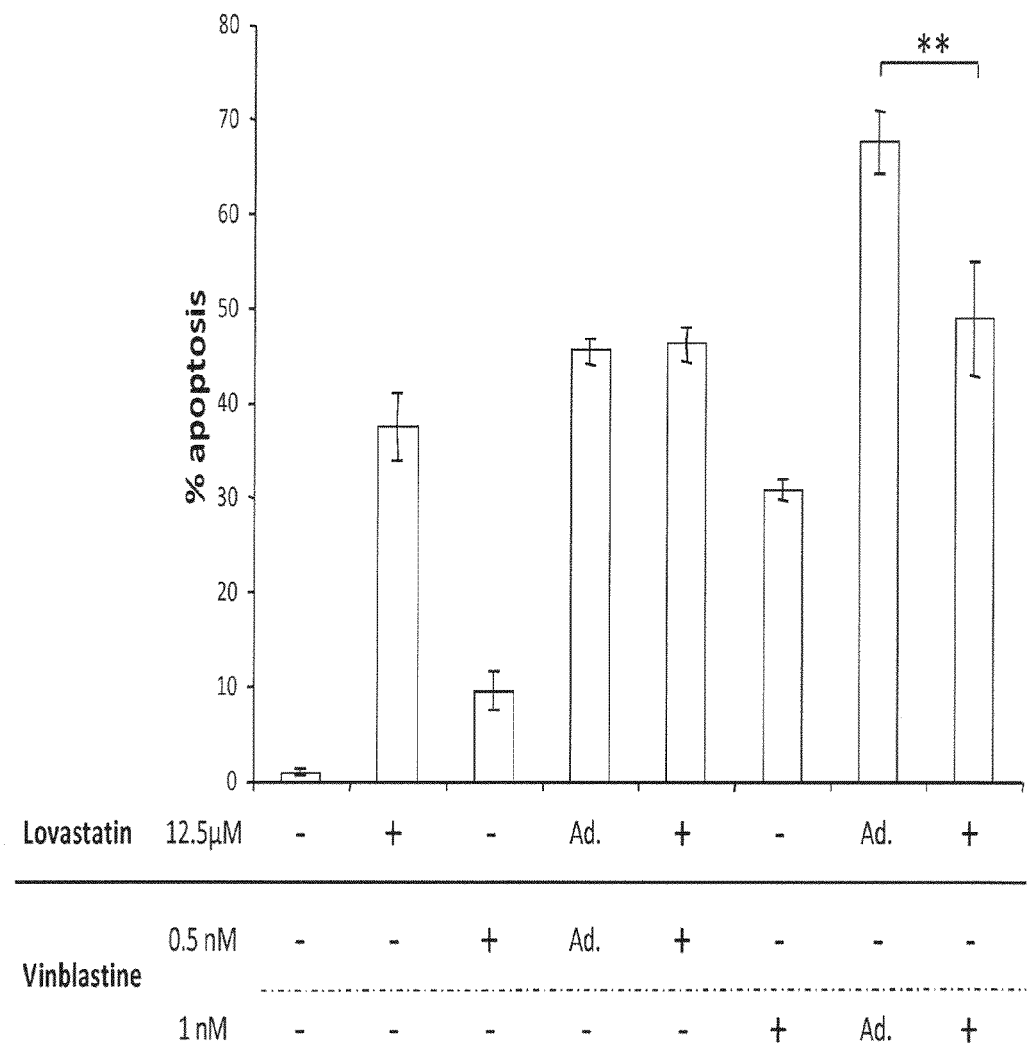

FIG. 5 Apoptosis induction by lovastatin and vinblastine in HGT-1 Cells

HGT-1 cells were treated with 12.5 µM lovastatin or with 0.5 or 1 nM vinblastine alone or in combination for 48 h. Apoptosis was determined by Hoechst 33342 staining. Values are means±S.D. (n=4). Ad: expected percentage from additive effects, addition of % apoptosis from lovastatin (12.5 µM)+vinblastine (0.5 or 1 nM). ** $P<0.01$ compared with the numerical addition of individual treatment (Student's t test).

Figure 6:
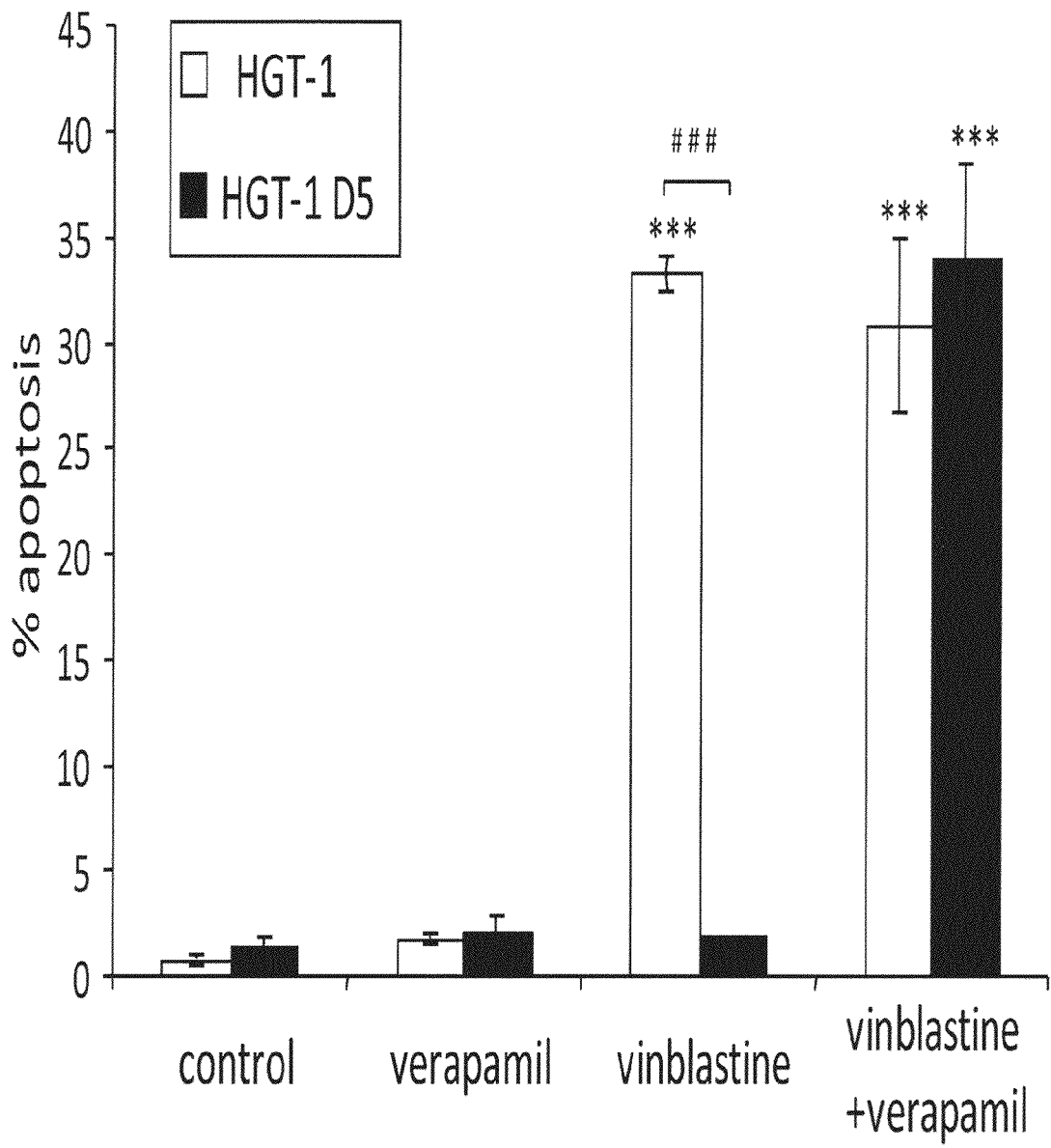

FIG. 6 Effect of vinblastine in HGT-1 and D5 cells

HGT-1 and docetaxel-resistant HGT-1 cells (named D5) were treated with 1 nM vinblastine alone or in combination with 20 µM verapamil for 48 h. Apoptosis was determined by Hoechst 33342 staining. Values are means±S.D. (n=3). *** $P<0.001$ compared with the control, ### $P<0.001$ D5 cells compared with HGT-1 cells (Student's t test).

FIG. 7 Comparison of the effect of lovastatin in HGT-1 and D5 cells.

(A) Apoptosis induction by lovastatin in HGT-1 and D5 cells. HGT-1 cells and docetaxel-resistant HGT-1 cells were treated with lovastatin for 48 or 72 h. Apoptosis was determined by Hoechst 33342 staining. Values are means±S.D (n=3). * $P<0.1$ or ** $P<0.01$ D5 cells compared with HGT-1 cells (Student's t test). (B) HGT-1 and D5 cells were treated with 2.5 µM Lovastatin for 72 h. Cyclin B1, D1, p21, p27, aurora kinase A,-B, Bax Bcl-2, Mcl-1 and survivin protein levels were analyzed by western-blotting. Hsc70 was used as a loading control. The western blotting analyses are representative of three experiments with similar results.

EXAMPLES

The following examples describe some of the preferred modes of making and practicing the present invention. However, it should be understood that the examples are for illustrative purposes only and are not meant to limit the scope of the invention.

Example 1

Material and Methods

Cell Culture

HGT-1 human gastric cancer cells were grown at 37° C. under a humidified atmosphere of 5% CO2 in DMEM (Dulbecco's modified Eagle's medium) (Lonza, Saint Beauzire, France), containing 4.5 g/L glucose and supplemented with 5% fetal bovine serum without antibiotics (Gibco-Invitrogen, Cergy Pontoise, France).

Selection of the docetaxel-resistant cell populations was performed with mass cultures grown in complete medium supplemented with 5 nM docetaxel. Massive cell death occurred for several weeks under continuous selective pressure, after which the populations stabilized and started to grow with no more signs of death. Cells were constantly grown in presence of 5 nM docetaxel, excepted for the cell passage that preceded the experiments that involved drug treatments.

Fluorescence In Situ Hybridization (FISH)

The number of MDR1 copies was determined by FISH with bacterial artificial chromosome (BAC) clones chosen from the human genome browser database of the Genome Bioinformatics Group at the University of California, Santa Cruz (http://www.genome.ucsc.edu/).

BACs RP11-806M4 and RP11-42N21 were extracted using standard methods and then labeled by nick translation in spectrum orange (Abbott, Rungis, France) and in spectrum green (Abbott), respectively.

Dual FISH using RP11-42N21 and RP11-806M4 was performed on HGT-1 and HGT-1-D5 cell lines according to standard procedures (Morel, Bris et al. 2003). After hybridization, the slides were counterstained with 4',6-diamidino-2-phenyl-indole. The slides were analyzed using a Zeiss Axio Plan microscope (Zeiss, Le Pecq, France). Subsequent image acquisition was performed using a CCD camera with Isis (significant in-situ imaging system) (MetaSystems, Altlussheim, Germany). For each cell line, at least 30 metaphases were analyzed.

Analysis of Apoptotic Chromatin Fragmentation

The cells were treated with different concentrations of docetaxel alone or with lovastatin. Apoptosis was determined by Hoechst 33342 (10 µg/ml in PBS) staining of the cells for 15 min at 37° C. and fluorescence microscopy analysis of 300 cells per condition, from replicate cultures.

RNA Extraction and RT (Reverse Transcription)-PCR Analysis

Total RNA was isolated using Trizol (Invitrogen, Cergy-Pontoise, france) and the RNA samples were used for the first-strand cDNA synthesis with the High Capacity cDNA Reverse Transcription kit and random hexamer primers (Applied biosystems). Quantitative real-time RT-PCR was performed using the Power SYBR Green Kit (Applied biosystems) according to the manufacturer's instructions. mRNA levels were analyzed in duplicate, normalized against GAPDH or phospho-protein P0 as an internal control gene. The results are expressed as the relative gene expression using the ΔΔCt method (Livak and Schmittgen 2001). The primer sequences and reaction conditions will be provided upon request.

Protein Extraction and Western Blotting Analysis

The cells were harvested, washed in PBS and lysed in ripa buffer (50 mM Tris HCl pH7.4, 150 mM NaCl, 0.5% Sodium deoxycholate, 0.1% SDS, 1% NP40, 1 mM EDTA, 1 mM PMSF) containing protease inhibitor cocktail (Roche, Meylan, France) and phosphatase inhibitor (Active motif) for 10 min at 4° C. Sixty micrograms of proteins were boiled in Laemmli sample buffer (Bio-Rad) for 5 min, separated by SDS-PAGE using 12% or 15% polyacrylamide gels and blotted onto polyvinyl difluoride membranes (GE Healthcare). Non specific binding sites were blocked for 1 h at room temperature by 5% (wt/v) fat-free milk before overnight incubation at 4° C. with specific rabbit (or mouse for cyclin B1) anti-human antibodies: aurora kinase A and B, procaspase-3, PARP, Bcl-2, Bax and survivin (Cell Signaling Technology-Ozyme, Saint Quentin en Yvelines, France), p27, p21, Mcl-1, cyclin B1 (Santa Cruz biotechnology, Tebu-bio, le Perray en Yvelines, France), cyclin D1 (NeoMarkers, Thermo Fisher Scientific, Illkirch, France) or HSC70 (Abcam, Paris, France) as a loading control. Anti-phospho-ERK1/2 was a mouse monoclonal antibody against a synthetic phosphopeptide (residues around threonine 202 and tyrosine 209 of human p44 MAPK, Cell Signaling Technology, Ozyme, France). Polyclonal antibodies against ERK1 (rabbit, sc-94) or ERK2 (rabbit, sc-154) and phospho-MEK1/2 were from Santa Cruz Biotechnology (Tebu-bio). Rabbit anti-phospho-JNK (Cell Signaling, Saint-Quentin en Yvelines, France) and rabbit polyclonal antibody anti-P38 (Santa Cruz Biotechnology, Tebu-bio). Primary antibodies were detected with a horseradish peroxidase-conjugated IgGs (GE Healthcare, Orsay, France). Blots were revealed using an Enhanced Chemiluminescence detection kit (GE Healthcare) by the Chemcapt™ software.

Example 2

Lovastatin, Docetaxel and Combinations Trigger HGT-1 Apoptosis

The inventors have shown previously that lovastatin could induce apoptosis of HGT-1 gastric cancer cells (Gibot L, 2009). As shown in FIG. 1, 35% apoptosis was attained in response to 12.5 µM lovastatin for 48 h. Docetaxel also induced apoptosis, although at a lower level (15% and 27% for 5 nM and 10 nM, respectively). That docetaxel-induced apoptosis was further demonstrated by the ability of the broad spectrum caspase inhibitor Z-VAD-fmk to suppress cell death. Strikingly, the exposure to both drugs had a synergistic effect (up to 80% apoptosis), when compared to the effect expected from the addition of % apoptosis obtained for the drugs used as single agents. Hence, docetaxel induced apoptosis in these gastric cancer cells, and its effect was enhanced by lovastatin.

Example 3

Lipid Synthesis Control is Impaired in Lovastatin- and Docetaxel-Treated Cells

To characterize the effects of the drugs on lipid synthesis genes, HGT-1 cells were treated by either molecule or by combinations of both for 48 h. Relative mRNA levels were determined by quantitative real time RT-PCR. The Low Density Lipoprotein Receptor (LDL-R), the HMG-CoA reductase, the Farnesyl Pyrophosphate Synthase (FPPS) and the Fatty Acyl Synthase (FAS) genes were all induced by lovastatin, but not by docetaxel. The exposure to both drugs showed inductive effects similar to those obtained for lovastatin alone.

Example 4

Proteolytic Cleavage of Apoptosis Proteins in Response to Drug Treatments

Caspase-3 and PARP were cleaved in response to lovastatin and docetaxel or combination of both drugs, further demonstrating apoptosis engagement (FIG. 2A). Pro-caspase-7 was also cleaved, especially for the highest drug concentrations.

The Mcl-1 gene encodes a major anti-apoptotic protein. All treatments triggered suppression of the protein (FIG. 2B). A short 19 kDa fragment appeared in response to treatment by the drugs, possibly as a result of apoptosis engagement, as z-VAD-fmk prevented its appearance. Bax, a major pro-apoptotic member of the Bcl-2 protein family was either slightly suppressed in presence of lovastatin or combination of the two drugs, or remained unchanged in response to docetaxel.

These results indicate that the apoptosis sensitizing activity of the drugs can be contributed, at least in part, by a decrease in the level of the Mcl-1 and, to a lesser extent, Bcl-2, proteins.

Example 5

Cell Cycle and Mitosis Impairment

Since docetaxel hampers mitosis, the inventors sought to determine the effects of lovastatin and docetaxel on p21 and p27 transcript levels. As shown in FIG. 3A, both drugs induced p21 expression, with a more marked effect (up to 4-fold) with lovastatin than for docetaxel. The drug combination led to a higher effect (up to 7-fold for 10 nM docetaxel plus lovastatin) than obtained for the drugs used as single agents. These increases in p21 transcript were associated with a parallel increase in p21 protein. The expression of p27 was slightly reduced by lovastatin or drug combinations. These data indicate that lovastatin and docetaxel had comparable abilities to suppress cell division through up-regulation of the cell cycle inhibitor p21. In order to analyze the effects of the drugs on proteins involved in mitosis progression, the inventors next looked at expression of cyclin B1, cyclin D1 and aurora kinase A. As shown in FIG. 4A, lovastatin reduced expression of all transcripts, either alone or when combined with docetaxel. In addition, lovastatin repressed aurora kinase B and survivin, even more strongly than cyclin B1, cyclin D1 and aurora kinase A mRNAs, either alone or combined with docetaxel, although docetaxel weakly induced these transcripts (FIG. 4B). In addition, lovastatin alone or in combination with docetaxel triggered a decrease in all proteins. Docetaxel also triggered a decrease in these proteins, with the exception of cyclin B1, which expression was slightly increased (FIG. 4C). Strikingly, docetaxel strongly induced survivin levels. However, lovastatin blocked this inducing effect, and even suppressed the protein under the combination of both drugs at the highest concentration. These results show that the combination of lovastatin suppressed expression of all these proteins and, especially, lovastatin opposed the effects of docetaxel.

Finally, the inventors analyzed expression of the JNK, p38 and ERK pathways in response to lovastatin and docetaxel. The phosphorylated form of the jun kinase was induced in presence of lovastatin, alone or in combination, while docetaxel had no effect. Conversely, the levels of phosho-MEK1/2 and phosho-ERK1/2 were decreased by lovastatin, similarly to p38 MAP kinase, whereas docetaxel had no effect. These results were in good agreement with the ability of lovastatin to slow down cell cycle progression and trigger cell death through induction of stress pathways, especially through JNK, but not p38, activation.

Example 6

Effect of Vinblastine/Lovastatin Combination on Cell Death

As a control for the specificity of docetaxel, the inventors used vinblastine, which acts in the reverse way as docetaxel by inhibiting the re-polymerization of microtubules. As can be seen in FIG. 5, 1 nM vinblastine triggered about 30% apoptosis but did not add to the effect of lovastatin, even showing some antagonism over the expected death rate (for the 1 nM drug concentration). Hence, these observations clearly distinguished docetaxel from vinblastine, despite the fact that both drugs could efficiently trigger apoptosis of HGT-1 cells.

Example 7

Isolation of Docetaxel-resistant Cells

Drug resistance is a serious hurdle for the treatment of cancer patients. In order to look for novel ways to get around acquired resistance to docetaxel, the inventors first isolated a population derived form HGT-1 cells following several weeks of culture in the continuous presence of 5 nM docetaxel. As shown in FIG. 6, the D5 cell population was also resistant to vinblastine-induced apoptosis. This resistance was fully overcome in presence of verapamil, a P-glycoprotein (Pgp, the product of the MDR-1 gene) blocker, indicating that one major difference between HGT-1 and D5 cells was at the level of expression and function of Pgp. To verify that D5 cells over-expressed the MDR-1 gene, the inventors performed quantitative RT-PCR with MDR-1 primers. This analysis showed that the MDR-1 gene was dramatically over-expressed in D5 cells, whereas no signal could be obtained with the parental cells. In addition, the expression of the other members of the ABC transporters (MRP-1/2/3) was unchanged. Hence, these results demonstrate that the acquired resistance to docetaxel of D5 cells was due to a massive over-expression of Pgp. To fully confirm these data, the inventors performed a fish analysis using probes that cover the MDR-1 gene locus. Chromosome amplification was readily detected in 47.5% of mitotic figures of D5 but not HGT-1 cells, in support of the over-expression of MDR-1 transcript in D5 cells.

Example 8

Enhanced Apoptosis by Lovastatin in D5 Cells

Figure 7A:
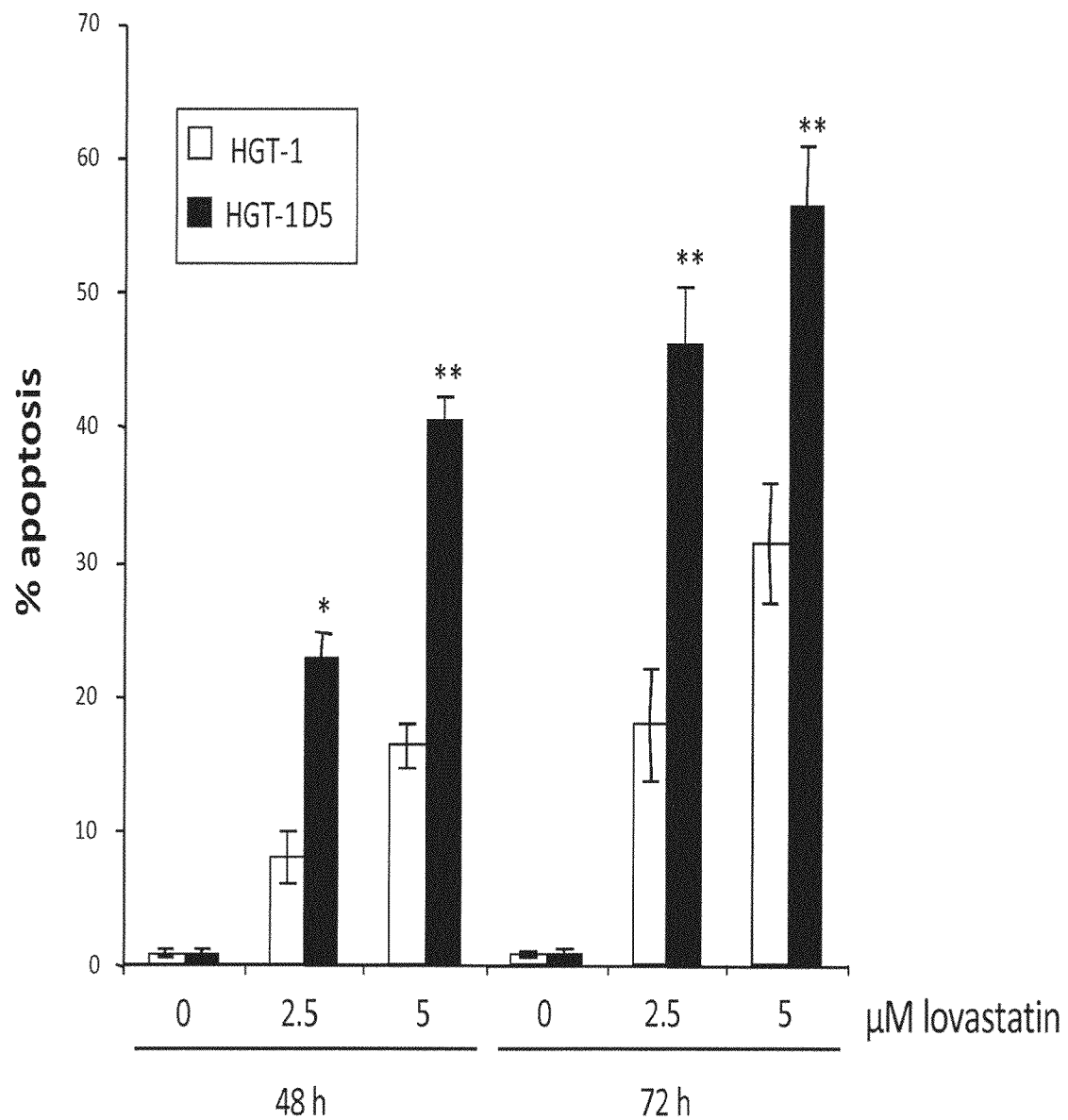
Figure 7B:
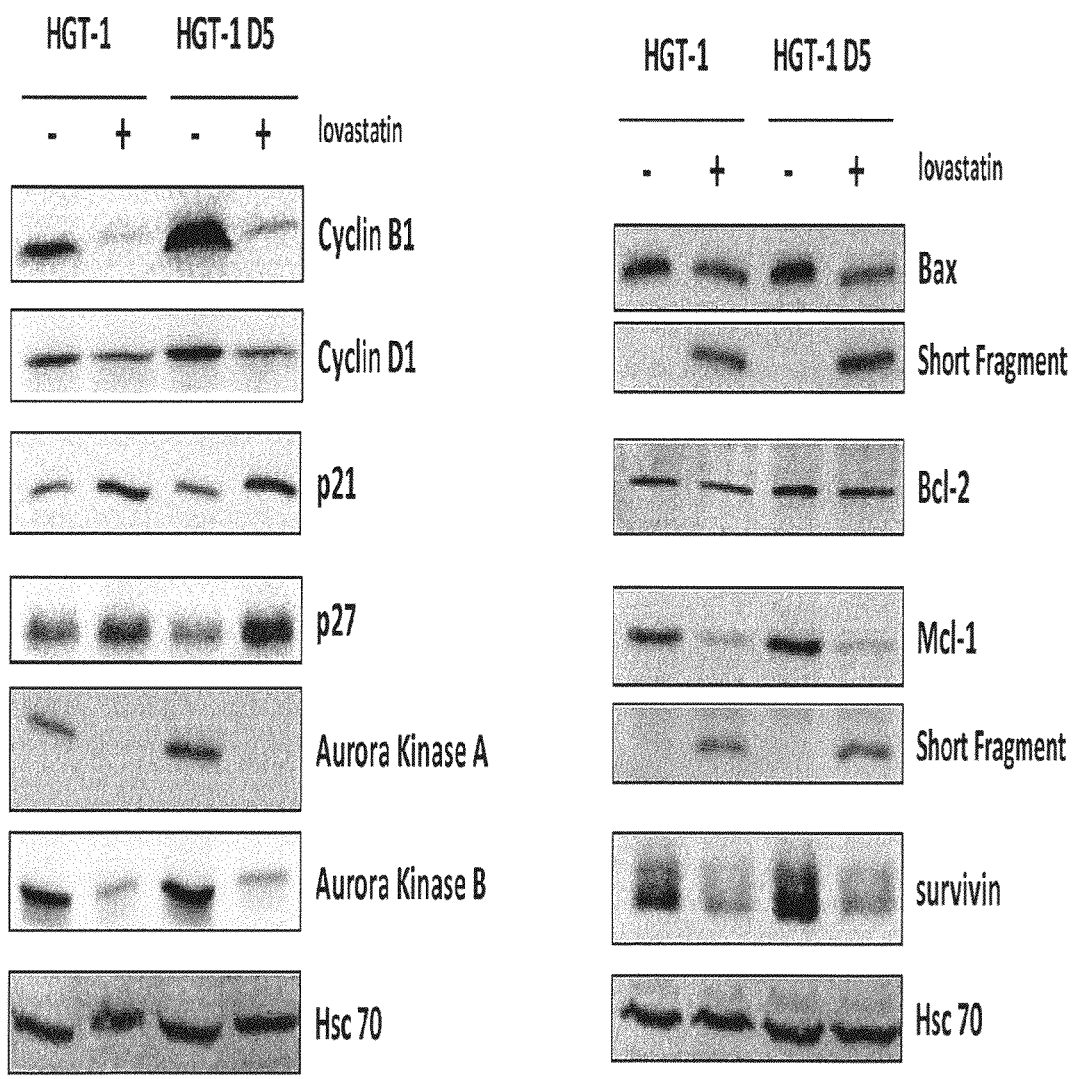

In order to determine the effect of lovastatin on D5 cells, the inventors treated the cells with either 2.5 or 5 µM lovastatin, i.e. drug concentrations lower than those used for the initial part of the study, for 48 or 72 h. As shown in FIG. 7A, both concentrations triggered a dose- and time-dependent increase in apoptosis in HGT-1 cells (up to 32%). Strikingly, D5 cells were much more sensitive to lovastatin than HGT-1 cells (up to 55%). To further characterize the docetaxel-resistant cells the inventors performed western-blotting analyses. As show in FIG. 7B, protein levels were comparable between HGT-1 and D5 cells, except for cyclin B1 and survivin, which were increased in D5 cells. Lovastatin reduced (cyclin D1, aurora kinases, Bax, Bcl-2, Mcl-1) or induced (p21) protein levels similarly in HGT-1 and D5 cells. Over-expression of survivin and cyclin B1 proteins in D5 cells was fully suppressed by lovastatin. In addition, lovastatin induced p27 in D5 cells, adding a further level of cell cycle blockade. Taken together, these results show that acquired resistance to docetaxel was not associated with a reduced ability to undergo lovastatin-dependent apoptosis or to an inability of lovastatin to influence target protein expression. Even though cell cycle-associated cyclin B1 and survivin were expressed at higher levels in D5 cells, this was abolished by lovastatin treatment.

Discussion

In this study, the inventors have analyzed the effects of docetaxel and lovastatin on the human gastric cancer cell line HGT-1. The results showed that docetaxel was able to induce apoptosis, an effect that proved to be synergistic with that of lovastatin, a potent apoptosis inducer in these cells, as the inventors had shown previously (Gibot, Follet et al. 2009). Lipid synthesis control was not affected by docetaxel, unlike lovastatin, as anticipated. Both docetaxel and lovastatin suppressed the anti-apoptotic Mcl-1 protein. Both drugs induced the cell cycle inhibitor p21 mRNA and protein, and even stronger effects were obtained upon addition of both drugs. Protein levels of cyclin B1, D1, aurora kinases A and B, important determinants of cell cycle progression, were slightly reduced or unchanged under docetaxel treatment, but strongly reduced by lovastatin, used alone or in combination with docetaxel, suggesting that lovastatin could also regulate negatively expression of genes directly involved in mitosis. Moreover, the inventors showed for the first time a clear link between statins and aurora kinases expression, at both mRNA and protein levels. Further experiments will be needed to explore more precisely pathways involved in aurora kinases repression under statin treatment. In addition, docetaxel induced survivin expression, despite triggering apoptosis. Therefore, it appears that docetaxel may have somewhat contradictory effects with respect to cell death and cell division control as it may stimulate both pro-death and pro-survival pathways. By contrast, lovastatin opposed docetaxel to suppress survivin induction and promote cell death. In addition, the caspase-mediated cleavage of Mcl-1 and Bax proforms, mainly resulting from lovastatin treatment, alone or combined, could amplify the apoptotic response.

As an approach to identify new ways to get around established resistance to docetaxel, the inventors isolated an HGT-1 derivative cell line that was stably resistant to 5 nM docetaxel. This phenotype was due to the amplification of the MDR1 gene locus that encodes Pgp, a specific membrane transporter protein that is responsible for the expulsion of many drugs, restricting their active concentration and thus functional activity within cells. None of the other tested members of this protein subfamily was modified in these cells. Strikingly, cyclin B1 and survivin proteins were more expressed in D5 cells than in HGT-1 cells. When treated with lovastatin at low concentrations (2.5 and 5 µM), the resistant cells proved to be exquisitely sensitive to apoptosis induction, significantly more than HGT-1 parental cells. Furthermore, the induction of p21 mRNA by lovastatin was stronger in D5 cells (data not shown), and the level of p27 protein was raised in lovastatin-treated D5 cells. The responses of the other genes to the drugs were not different between D5 and HGT-1 cells. These results demonstrated that it was possible to overcome efficiently an acquired resistance to docetaxel in human gastric cancer cells upon using lovastatin at concentrations that are close to those attainable in serum.

This study brings in new lights into the mechanisms evoked by both docetaxel and lovastatin to reduce cell division and increase apoptotic cell death. Strikingly, the pro-death effects of lovastatin were always superior to the pro-survival effects triggered by docetaxel, although these were limited. Hence, it will be fair to assume that such a combination of compounds could offer new therapeutic options for the treatment of a solid tumor as gastric cancer. Furthermore, the data suggest that, should resistance to docetaxel occur—either spontaneously or as a result of treatments that lead to a stable MDR1 over-expression—this should be efficiently overcome through the use of lovastatin in adjuvant therapies. Moreover, the treatment of lovastatin-resistant HGT-1-derived cells (Gibot, Follet et al. 2009) by docetaxel triggered apoptosis at a higher level than that of HGT-1 parental cells (data not shown). The same reasoning as above can be made: in case of adaptation to statins—as may have occurred over years of statin therapy—the use of docetaxel could open new treatment options for human patients.

The cytotoxic activity of docetaxel has been attributed to its ability to stabilize the mitotic spindle, upon blocking microtubule polymerization. Direct consequences of this activity were a block of the cell cycle in the G2/M transition, or in subG1. Quite often, this was associated with an increase in p21. In addition, over-expression of p21 in docetaxel-resistant cells restored drug sensitivity (Canfield, Zhu et al. 2006). Interestingly, survivin gene expression was inducible by docetaxel in DU145 human prostate cancer cells (Kim, Chung et al. 2006), much like the inventors showed in HGT-1 cells. This observation could seem surprising, in view of the death potential of docetaxel treatment. However, Kim et al. showed that the increase in survivin was associated with the nuclear interaction with the pro-apoptotic Smac/DIABLO protein, which was proposed to promote cell death in this model (Kim, Chung et al. 2006). In addition, it was shown that cyclin B1 was able to promote docetaxel-induced apoptosis (Gomez, de Las Pozas et al. 2007), an effect that could participate in the induction of HGT-1 apoptosis, as cyclin B1 expression was slightly induced by docetaxel. Aurora kinases A and B proteins were reduced by docetaxel treatment of HGT-1 cells, in good agreement with previous studies in several cancer cell models that have clearly shown that inhibition of either kinase enhanced the cell killing activity of taxanes (Wang, Dong et al. 2009; Shimomura, Hasako et al. 2010). The results obtained here suggest that taxanes can directly suppress expression of these kinase genes in HGT-1 cells.

Drug combinations with taxanes have been reported to increase cell killing, as compared to the effects of single agents, either by combining dual cell death promoting activities (Bijnsdorp, Kruyt et al. 2008; Kucukzeybek, Gul et al. 2008; Kim, Lee et al. 2009; Reiner, de las Pozas et al. 2009) or by adding a drug efflux blocking activity to a cytotoxic effect (Miettinen, Grenman et al. 2009). The interplay between microtubule poisoning and impairment of the mevalonate pathway in our study also proved to be remarkably efficient to induce apoptotic cell death. These events were independent on p53 as HGT-1 cells carry an inactivating mutation in the gene (Sadji-Ouatas, Lasfer et al. 2002). These studies could be extended to gastric cancer cell lines that are p53 proficient, as roughly 65% of the reported p53 analyses in gastric cancers should be wild type (Lane 1999), and to the analysis of the in vivo response to the drug association of gastric cancer cells allowed to develop into tumours in immuno-compromised mice.

In summary, this study has shown the potential of the docetaxel+lovastatin combination for the efficient induction of gastric cancer cell death, both for cells sensitive or resistant to either drug, and may open the path to clinical trials for patients suffering from gastric cancers. The fact that statins are widely used in the human population without provoking significant deleterious effects would make this strategy readily acceptable, especially if the association allows usage of reduced amounts of either drug.

REFERENCES

Throughout this application, various references describe the state of the art to which this invention pertains. The disclosures of these references are hereby incorporated by reference into the present disclosure.

Agarwal, B., S. Bhendwal, et al. (1999). "Lovastatin augments apoptosis induced by chemotherapeutic agents in colon cancer cells." Clin Cancer Res 5(8): 2223-2229.

Baker, J., J. Ajani, et al. (2009). "Docetaxel-related side effects and their management." Eur J Oncol Nurs 13(1): 49-59.

Bijnsdorp, I. V., F. A. Kruyt, et al. (2008). "Synergistic interaction between trifluorothymidine and docetaxel is sequence dependent." Cancer Sci 99(11): 2302-2308.

Bjerre, L. M. and J. LeLorier (2001). "Do statins cause cancer? A meta-analysis of large randomized clinical trials." Am J Med 110(9): 716-723.

Canfield, S. E., K. Zhu, et al. (2006). "Bortezomib inhibits docetaxel-induced apoptosis via a p21-dependent mechanism in human prostate cancer cells." Mol Cancer Ther 5(8): 2043-2050.

Cerezo-Guisado, M. I., N. Garcia-Roman, et al. (2007). "Lovastatin inhibits the extracellular-signal-regulated kinase pathway in immortalized rat brain neuroblasts." Biochem J 401(1): 175-183.

Demidenko, Z. N., D. Halicka, et al. (2005). "Selective killing of adriamycin-resistant (G2 checkpoint-deficient and MRP1-expressing) cancer cells by docetaxel." Cancer Res 65(10): 4401-4407.

Demierre, M. F., P. D. Higgins, et al. (2005). "Statins and cancer prevention." Nat Rev Cancer 5(12): 930-942.

Ferlay, J., D. M. Parkin, et al. (2010). "Estimates of cancer incidence and mortality in Europe in 2008." Eur J Cancer 46(4): 765-781.

Gomez, L. A., A. de Las Pozas, et al. (2007). "Increased expression of cyclin B1 sensitizes prostate cancer cells to apoptosis induced by chemotherapy." Mol Cancer Ther 6(5): 1534-1543.

Graaf, M. R., D. J. Richel, et al. (2004). "Effects of statins and farnesyltransferase inhibitors on the development and progression of cancer." Cancer Treat Rev 30(7): 609-641.

Gray-Bablin, J., S. Rao, et al. (1997). "Lovastatin induction of cyclin-dependent kinase inhibitors in human breast cells occurs in a cell cycle-independent fashion." Cancer Res 57(4): 604-609.

Holstein, S. A. and R. J. Hohl (2001). "Synergistic interaction of lovastatin and paclitaxel in human cancer cells." Mol Cancer Ther 1(2): 141-149.

Katz, M. S. (2005). "Therapy insight: Potential of statins for cancer chemoprevention and therapy." Nat Clin Pract Oncol 2(2): 82-89.

Kim, J. Y., J. Y. Chung, et al. (2006). "Nuclear interaction of Smac/DIABLO with Survivin at G2/M arrest prompts docetaxel-induced apoptosis in DU145 prostate cancer cells." Biochem Biophys Res Commun 350(4): 949-954.

Kim, S. M., S. Y. Lee, et al. (2009). "Inhibition of NF-kappaB by ginsenoside Rg3 enhances the susceptibility of colon cancer cells to docetaxel." Arch Pharm Res 32(5): 755-765.

Kozar, K., R. Kaminski, et al. (2004). "Cerivastatin demonstrates enhanced antitumor activity against human breast cancer cell lines when used in combination with doxorubicin or cisplatin." Int J Oncol 24(5): 1149-1157.

Kucukzeybek, Y., M. K. Gul, et al. (2008). "Enhancement of docetaxel-induced cytotoxicity and apoptosis by all-trans retinoic acid (ATRA) through downregulation of survivin (BIRC5), MCL-1 and LTbeta-R in hormone- and drug resistant prostate cancer cell line, DU-145." J Exp Clin Cancer Res 27: 37.

Laboisse, C. L., C. Augeron, et al. (1982). "Characterization of a newly established human gastric cancer cell line HGT-1 bearing histamine H2-receptors." Cancer Res 42(4): 1541-1548.

Lane, D. P. (1999). "Exploiting the p53 pathway for cancer diagnosis and therapy." Br J Cancer 80 Suppl 1: 1-5.

Liu, H., S. L. Liang, et al. (2009). "Statins induce apoptosis in ovarian cancer cells through activation of JNK and enhancement of Bim expression." Cancer Chemother Pharmacol 63(6): 997-1005.

Livak, K. J. and T. D. Schmittgen (2001). "Analysis of relative gene expression data using real-time quantitative PCR and the 2(-Delta Delta C(T)) Method." Methods 25(4): 402-408.

Martirosyan, A., J. W. Clendening, et al. (2010). "Lovastatin induces apoptosis of ovarian cancer cells and synergizes with doxorubicin: potential therapeutic relevance." BMC Cancer 10: 103.

Miettinen, S., S. Grenman, et al. (2009). "Inhibition of P-glycoprotein-mediated docetaxel efflux sensitizes ovarian cancer cells to concomitant docetaxel and SN-38 exposure." Anticancer Drugs 20(4): 267-276.

Moasser, M. M., L. Sepp-Lorenzino, et al. (1998). "Farnesyl transferase inhibitors cause enhanced mitotic sensitivity to taxol and epothilones." Proc Natl Acad Sci USA 95(4): 1369-1374.

Morel, F., M. J. Bris, et al. (2003). "Double minutes containing amplified bcr-abl fusion gene in a case of chronic myeloid leukemia treated by imatinib." Eur J Haematol 70(4): 235-239.

Nishiyama, M. and S. Wada (2009). "Docetaxel: its role in current and future treatments for advanced gastric cancer." Gastric Cancer 12(3): 132-141.

Pfefferkorn J A. (2011) "Novel 3-hydroxy-3-methylglutaryl-coenzyme A reductase inhibitors: a patent review. Expert Opin Ther Pat.; 21(2):187-203

Reiner, T., A. de las Pozas, et al. (2009). "Low dose combinations of 2-methoxyestradiol and docetaxel block prostate cancer cells in mitosis and increase apoptosis." Cancer Lett 276(1): 21-31.

Sadji-Ouatas, Z., M. Lasfer, et al. (2002). "Doxorubicin and octreotide induce a 40 kDa breakdown product of p53 in human hepatoma and tumoral colon cell lines." Biochem J 364 (Pt 3): 881-885.

Sane, K. M., M. Mynderse, et al. (2010). "A novel geranylgeranyl transferase inhibitor in combination with lovastatin inhibits proliferation and induces autophagy in STS-26T MPNST cells." J Pharmacol Exp Ther 333(1): 23-33.

Sassano, A. and L. C. Platanias (2008). "Statins in tumor suppression." Cancer Lett 260 (1-2): 11-19.

Schimming, R., K. A. Mason, et al. (1999). "Lack of correlation between mitotic arrest or apoptosis and antitumor effect of docetaxel." Cancer Chemother Pharmacol 43(2): 165-172.

Shimomura, T., S. Hasako, et al. (2010). "MK-5108, a highly selective Aurora-A kinase inhibitor, shows antitumor activity alone and in combination with docetaxel." Mol Cancer Ther 9(1): 157-166.

Taylor-Harding, B., S. Orsulic, et al. (2010). "Fluvastatin and cisplatin demonstrate synergistic cytotoxicity in epithelial ovarian cancer cells." Gynecol Oncol.

van der Spek, E., A. C. Bloem, et al. (2009). "Inhibition of the mevalonate pathway potentiates the effects of lenalidomide in myeloma." Leuk Res 33(1): 100-108.

Wang, X., L. Dong, et al. (2009). "Stable knockdown of Aurora-A by vector-based RNA interference in human esophageal squamous cell carcinoma cell line inhibits tumor cell proliferation, invasion and enhances apoptosis." Cancer Biol Ther 8(19): 1852-1859.

Zheng, X., X. X. Cui, et al. (2010). "Atorvastatin and celecoxib in combination inhibits the progression of androgen-dependent LNCaP xenograft prostate tumors to androgen independence." Cancer Prey Res (Phila) 3(1): 114-124.

The invention claimed is:

1. A method of enhancing sensitivity of a patient suffering from a gastric cancer to a taxane, comprising
administering to said patient an amount of a statin sufficient to sensitize said patient to said taxane; and
administering to said patient a therapeutically effective amount of a taxane to treat said gastric cancer after said patient is sensitized to said taxane.

2. The method of claim 1, wherein said statin is lovastatin.

3. The method of claim 1, wherein said taxane is docetaxel.

* * * * *